(12) United States Patent
Shimada et al.

(10) Patent No.: US 12,213,860 B2
(45) Date of Patent: Feb. 4, 2025

(54) METHOD FOR SEPARATING MAMMALIAN SPERM, ARTIFICIAL INSEMINATION METHOD, AND IN VITRO FERTILIZATION METHOD

(71) Applicant: Hiroshima University, Higashihiroshima (JP)

(72) Inventors: Masayuki Shimada, Hiroshima (JP); Takashi Umehara, Hiroshima (JP); Masaaki Goto, Oita (JP); Moeka Kugumiya, Oita (JP)

(73) Assignee: Hiroshima University, Higashihiroshima (JP)

( * ) Notice: Subject to any disclaimer, the term of this patent is extended or adjusted under 35 U.S.C. 154(b) by 1229 days.

(21) Appl. No.: 16/627,660

(22) PCT Filed: Jun. 26, 2018

(86) PCT No.: PCT/JP2018/024206
§ 371 (c)(1),
(2) Date: Dec. 30, 2019

(87) PCT Pub. No.: WO2019/004217
PCT Pub. Date: Jan. 3, 2019

(65) Prior Publication Data
US 2020/0129280 A1    Apr. 30, 2020

(30) Foreign Application Priority Data

Jun. 30, 2017 (JP) ................ 2017-129768
Jun. 25, 2018 (JP) ................ 2018-120260

(51) Int. Cl.
| A61D 19/02 | (2006.01) |
| C12N 5/076 | (2010.01) |
| G01N 1/40  | (2006.01) |

(52) U.S. Cl.
CPC ............ *A61D 19/02* (2013.01); *C12N 5/061* (2013.01); *G01N 1/4077* (2013.01); *C12N 2501/999* (2013.01)

(58) Field of Classification Search
CPC combination set(s) only.
See application file for complete search history.

(56) References Cited

U.S. PATENT DOCUMENTS

| 2004/0038356 A1 | 2/2004 | Pertoft |
| 2004/0055030 A1 | 3/2004 | Maxwell et al. |
| 2004/0088745 A1 | 5/2004 | Robl et al. |
| 2010/0222196 A1 | 9/2010 | Ito |

FOREIGN PATENT DOCUMENTS

| CN | 1681921 A | 10/2005 |
| CN | 101024829 A | 8/2007 |
| CN | 103784440 A | 5/2014 |
| JP | H06181666 A | 7/1994 |
| JP | H07163269 A | 6/1995 |
| JP | 2004516035 A | 6/2004 |
| JP | 2008022760 A | 2/2008 |
| JP | 2009119457 A | 6/2009 |
| WO | 2015/125013 A1 | 8/2015 |
| WO | 2019/004217 A1 | 1/2019 |

OTHER PUBLICATIONS

Heil, Florian, et al. "Species-specific recognition of single-stranded RNA via toll-like receptor 7 and 8." Science 303.5663: 1526-1529. (Year: 2004).*
"Specialty Definition: Hypergravity". Websters Online Dictionary. Retrieved (Year: Apr. 29, 2011).*
Koundouros, Sawas, and P. Verma. "Significant enrichment of Y-bearing chromosome human spermatozoa using a modified centrifugation technique." International journal of andrology 35.6: 880-886. (Year: 2012).*
Zhu, Xingxing, et al. "TLR signalling affects sperm mitochondrial function and motility via phosphatidylinositol 3-kinase and glycogen synthase kinase-3α." Cellular Signalling 28.3: 148-156. (Year: 2016).*
Padilla, A. W., and R. H. Foote. "Extender and centrifugation effects on the motility patterns of slow-cooled stallion spermatozoa." Journal of animal science 69.8: 3308-3313. (Year: 1991).*
Extended European Search Report, dated Apr. 21, 2020, for corresponding European patent application No. 18824434.7.
Zhu et al., TLR signalling affects sperm mitochondrial function and motility via phosphatidylinositol 3-kinase and glycogen synthase kinase-3alpha. Cellular Signalling, vol. 28, No. 3., pp. 148-156 (2015).
Umehara et al., Activation of Toll-like receptor 7/8 encoded by the X chromosome alters sperm motility and provides a novel simple technology for sexing sperm. PLoS Biology, vol. 17, No. 8, e300398 (2019).
Office Action dated Oct. 9, 2022, issued in corresponding Chinese patent application No. 201880042257.X (original and English translation enclosed).
Koundouros, S. et al., "Significant enrichment of Y-bearing chromosome human spermatozoa using a modified centrifugation technique", Int J Androl., vol. 35, No. 6, pp. 880-886 (2012).

(Continued)

*Primary Examiner* — Teresa E Knight
(74) *Attorney, Agent, or Firm* — K&L Gates LLP; Brian J. Novak; Giorgios N. Kefallinos (57) ABSTRACT

Provided are a method for separating mammalian sperm, by which even a large amount of sperm can be separated in a short time and decrease in motility of the separated sperm can be prevented; and an artificial insemination method, and an in vitro fertilization method. The method for separating mammalian sperm includes incubating the sperm in a medium containing a TLR7 ligand, and separating them into sperm floating in the upper layer and sperm sinking in the lower layer of the medium. The artificial insemination and in vitro fertilization methods include artificial insemination or in vitro fertilization for a non-human mammal using sperm of the non-human mammal separated by the method for separating mammalian sperm.

9 Claims, 5 Drawing Sheets

(56) References Cited

OTHER PUBLICATIONS

Mar. 7, 2014, entire text [retrieval date Dec. 18, 2015], non-official translation (Yamashita, Kenichi, "In-situ treatment technology for sperm", increasing success rate of artificial insemination (AI) in animal breeding—of collecting healthy sperms and separating genders, Materials distributed on the day in new technology briefing session from JST.
Saeidi, S. et al., "Sperm protection in the male reproductive tract by Toll-like receptors", Andrologia, 2014, vol. 46, No. 7, pp. 784-790.
International Search Report and Written Opinion mailed on Sep. 18, 2018 for International Patent Application Serial No. PCT/JP2018/024206 filed on Jun. 26, 2018.

* cited by examiner

*: SIGNIFICANTLY DIFFERENT FROM THE CONTROL

*: SIGNIFICANTLY DIFFERENT FROM THE CONTROL

METHOD FOR SEPARATING MAMMALIAN SPERM, ARTIFICIAL INSEMINATION METHOD, AND IN VITRO FERTILIZATION METHOD

CROSS REFERENCE TO RELATED APPLICATION(S)

This application is a national phase filing of PCT/JP2018/024206, filed on Jun. 26, 2018, which claims priority to Japanese Patent Application No. 2018-120260, filed on Jun. 25, 2018, and Japanese Patent Application No. 2017-129768, filed on Jun. 30, 2017, the entire disclosures of which are incorporated herein by reference.

TECHNICAL FIELD

The present disclosure relates to a method for separating mammalian sperm, an artificial insemination method, and an in vitro fertilization method.

BACKGROUND ART

Technology for gender preselection in domestic animals greatly contributes to the efficient production of the domestic animals. In the case of cow, for example, planed preselection for female can result in a succeeding cow. Meanwhile, cows must always be pregnant to produce milk. After producing succeeding cows, the mother cow receives a fertilized egg from Japanese Black, whose offspring is high-priced, to produce Japanese Black cattle, which greatly improves the management of dairy farmers. Regarding the price of Japanese Black calves, there is great difference in price between female and male, and the price of male calves is higher than that of female calves. Thus, a technology is demanded not only for cows to ensure production of succeeding cows (female offspring), but also for in vitro fertilization or artificial insemination after obtaining succeeding cows to obtain fertilized eggs from Japanese Black cattle and produce male calves.

As for pig farming, castrated males grow more quickly and reach a shipping weight in a shorter fattening period than females. Increasing the number of male offspring in hog production not only will improve the management of pig farming, but also will increase the pork production per feed, leading to an increase in food production worldwide. Since, however, there is criticism against castration, there remains a demand for selective production of female offspring.

As described above, technology for gender preselection in mammals, including domestic animals, is highly demanded. Known technologies for gender preselection include methods disclosed in Patent Literature 1 to 3. Besides them, a method focusing on the difference in size between X and Y chromosomes has been known. This method uses a well-established technology, a cell sorter, to sort sperm that have incorporated a fluorescent dye for staining DNA based on their fluorescence values, thereby separating off sperm having an X chromosome into a percentage of 90% or higher. This technology has been used in cow production.

CITATION LIST

Patent Literature

Patent Literature 1: Unexamined Japanese Patent Application Kokai Publication No. 2008-022760

Patent Literature 2: Unexamined Japanese Patent Application Kokai Publication No. H7-163269

Patent Literature 3: Unexamined Japanese Patent Application Kokai Publication No. H6-181666

SUMMARY OF INVENTION

Technical Problem

However, the method using a cell sorter has a problem of taking time to process a large amount of sperm. Furthermore, because of fluorescent staining and exposure to a special wavelength light, separated sperm have decreased motility, resulting in poor fertilization rate.

In view of the above, the present disclosure aims to provide a method for separating mammalian sperm, by which even a large amount of sperm can be separated in a short time and decrease in motility of the separated sperm can be prevented; and an artificial insemination method, and an in vitro fertilization method.

Solution to Problem

According to a first aspect of the present disclosure, there is provided a method for separating mammalian sperm, the method including:

incubating the sperm in a medium containing a TLR7 ligand; and separating the sperm into sperm floating in the upper layer and sperm sinking in the lower layer of the medium.

Preferably, the TLR7 ligand is at least one selected from the group consisting of resiquimod, imiquimod, gardiquimod, and loxoribine.

Further, the TLR7 ligand is preferably added in an amount from 0.03 to 30 μM.

Preferably, the separation is achieved by hypergravity load.

Preferably, the hypergravity load is generated by a centrifugal force.

Preferably, the centrifugal force to be loaded is more than 0×g and less than 100×g.

Preferably, 30% of the upper layer of the medium is collected to obtain a sperm population rich in Y chromosome-bearing sperm.

Preferably, 30% of the lower layer of the medium is collected to obtain a sperm population rich in X chromosome-bearing sperm.

According to a second aspect of the present disclosure, there is provided an artificial insemination method, including:

performing artificial insemination for a non-human mammal using sperm of the non-human mammal, wherein the sperm are separated by the method for separating mammalian sperm according to the first aspect of the present disclosure.

According to a third aspect of the present disclosure, there is provided an in vitro fertilization method, including:

performing in vitro fertilization for a non-human mammal using sperm of the non-human mammal, wherein the sperm are separated by the method for separating mammalian sperm according to the first aspect of the present disclosure.

Advantageous Effects of Invention

The method for separating mammalian sperm according to the present disclosure can separate a large amount of sperm in a short time while preventing decrease in motility of the separated sperm.

DESCRIPTION OF EMBODIMENTS

The method for separating mammalian sperm according to the present embodiment includes incubating sperm in a medium containing a TLR7 ligand. The method also includes thereafter separating the sperm into sperm floating in the upper layer and sperm sinking in the lower layer of the medium.

When sperm are incubated in a medium containing a TLR7 ligand, sperm without Y chromosome (hereinafter referred to as "X chromosome-bearing sperm") show decreased sperm activity, sinking to the lower layer of the medium. On the other hand, the activity of sperm with Y chromosome (hereinafter referred to as "Y chromosome-bearing sperm") is less likely to be decreased, so that they float in the upper layer of the medium.

Then, the sperm floating in the upper layer of the medium can be collected to obtain a sperm population rich in Y chromosome-bearing sperm. The sperm may be collected by a known technique capable of collecting the sperm population floating in the upper layer of the medium, including collection with a collection tool, such as a dropper. The collected sperm population mainly contains Y chromosome-bearing sperm, and the Y chromosome-bearing sperm fertilize an egg to produce a fertilized egg having XY chromosomes. Thus, artificial insemination or in vitro fertilization in mammals using the collected sperm population can selectively produce male offspring.

On the other hand, the sperm population sinking in the lower layer of the medium can be collected to obtain a sperm population rich in X chromosome-bearing sperm. The collected sperm population mainly contains X chromosome-bearing sperm, and the X chromosome-bearing sperm fertilize an egg to produce a fertilized egg having XX chromosomes. Thus, artificial insemination or in vitro fertilization in mammals using the collected sperm population can selectively produce female offspring.

The medium containing a TLR7 ligand can be prepared by adding the TLR7 ligand to a basal medium. The basal medium may be a medium that can be commonly used in incubation of sperm of mammals. Preferred examples of the basal medium include embryo culture media, such as HTF medium (composition: NaCl, KCl, $KH_2PO_4$, $MgSO_4.7H_2O$, $CaCl_2.2H_2O$, $NaHCO_3$, glucose, Na-pyruvate, Na-lactate, gentamicin sulfate salt, Phenol Red).

Examples of the TLR7 ligand include resiquimod, imiquimod, gardiquimod, and loxoribine. The TLR7 ligands may be used alone or in combination of two or more thereof.

The amount of the TLR7 ligand added to the basal medium may be determined as appropriate depending on the type of the TLR7 ligand to be used and the type of the animal to be used from which the sperm is derived, and is preferably from 0.03 μM to 30 μM. For example, when resiquimod is used to mouse sperm, resiquimod is preferably added in an amount from 0.3 μM to 3 μM. When used to bovine sperm, the preferred concentration is from 0.03 μM to 0.3 μM for resiquimod, and from 0.03 μM to 30 μM for imiquimod.

The incubation period is not particularly limited as long as it is sufficient to decrease the activity of X chromosome-bearing sperm and allow them to sink to the lower layer of the medium, and then to separate off Y chromosome-bearing sperm floating in the upper layer. For example, the incubation period is preferably from 30 minutes to 3 hours, more preferably from 1 to 2 hours.

Preferably, the separation is made by loading hypergravity. Sperm have a nature for swimming against the current. Thus, under hypergravity load, sperm are likely to swim against the direction of the loaded hypergravity. As described above, the activity of X chromosome-bearing sperm is decreased in a medium containing a TLR7 ligand. When hypergravity is loaded in such a situation, the X chromosome-bearing sperm cannot resist the hypergravity and tend to sink in the direction toward which the hypergravity is loaded, or to the lower layer of the medium. On the other hand, Y chromosome-bearing sperm, which are less likely to be affected by the TLR7 ligand, can swim, under hypergravity load, against the direction of the loaded hypergravity. Thus, the Y chromosome-bearing sperm can float in the upper layer of the medium. Therefore, separation by hypergravity load can increase the separation accuracy between Y chromosome-bearing sperm and X chromosome-bearing sperm.

A preferred method for loading hypergravity is by loading a centrifugal force, or centrifugation. The centrifugal force to be loaded is preferably more than 0×g and less than 100×g, more preferably 50×g. When the loaded centrifugal force (hypergravity) is too large, even Y chromosome-bearing sperm cannot resist the hypergravity, sinking to the lower layer of the medium. On the other hand, when the centrifugal force (hypergravity) is too small, some Y chromosome-bearing sperm may also swim to the lower layer of the medium, resulting in lowered separation effect.

The time for loading the hypergravity may be a time for separating the X chromosome-bearing sperm and the Y chromosome-bearing sperm, and is about 30 minutes, for example, depending on the hypergravity to be loaded.

Preferably, the sperm population rich in Y chromosome-bearing sperm floating in the upper layer, preferably 30% of the upper layer, of the medium, is collected and used for artificial insemination or in vitro fertilization. In addition, the sperm population rich in X chromosome-bearing sperm sinking in the lower layer, preferably 30% of the lower layer, of the medium, is preferably collected and used for artificial insemination or in vitro fertilization. This is because the middle layer of the medium is likely to contain Y chromosome-bearing sperm and X chromosome-bearing sperm in combination. It is noted that the collected sperm population is washed with the basal medium or the like before use.

The method for separating mammalian sperm according to the present embodiment is by incubating sperm in a medium containing a TLR7 ligand as described above, and thus can process a large amount of sperm in a short time.

The method for separating mammalian sperm according to the present embodiment does not stain sperm with a fluorescent substance or expose sperm to a special wavelength light. Thus, the method can prevent the activity of the separated sperm from being decreased and thus prevent the fertilization rate from being decreased.

When artificial insemination or in vitro fertilization is performed using the separated sperm population rich in Y chromosome-bearing sperm or sperm population rich in X chromosome-bearing sperm, a usual method for artificial insemination or in vitro fertilization may be performed using the separated sperm. Artificial insemination or in vitro fertilization using the sperm population rich in Y chromosome-bearing sperm can selectively produce male offspring. On the other hand, artificial insemination or in vitro fertilization using the sperm population rich in X chromosome-bearing sperm can selectively produce female offspring.

EXAMPLES (Transcriptome Analysis of Mouse Sperm)

Transcriptome analysis was performed for a mouse sperm. RNA fragments in a mouse sperm were extracted and the total RNA was analyzed with a sequencer. 1467 genes derived from the X chromosome were expressed, and 26 of them were RNAs encoding receptors. The 26 RNAs are shown in Table 1.

TABLE 1

| gene | expression |
| --- | --- |
| Pgrmc1 | 2.30 |
| P2ry10 | 1.63 |
| Il2rg | 1.59 |
| Tlr8 | 0.43 |
| Ar | 0.37 |
| Tlrl3 | 0.36 |
| Il13ra1 | 0.34 |
| Htr2c | 0.31 |
| Gpr174 | 0.28 |
| Cysltr1 | 0.26 |
| Tlr7 | 0.25 |
| Gria3 | 0.20 |
| Gpr34 | 0.19 |
| Gabra3 | 0.19 |
| Gabre | 0.15 |

TABLE 1-continued

| gene | expression |
| --- | --- |
| Gpr64 | 0.13 |
| Il13ra2 | 0.12 |
| Eda2r | 0.12 |
| Grpr | 0.08 |
| Avpr2 | 0.08 |
| Gabrq | 0.05 |
| Glra4 | 0.05 |
| Gpr143 | 0.05 |
| Glra2 | 0.04 |
| Lpar4 | 0.03 |
| Brs3 | 0.02 |

In the list, TLR7 is known to have a specific ligand that does not directly bind to the receptors encoded in autosome, and to release $Ca^{2+}$ with a stimulation. $Ca^{2+}$ is known to significantly affect the motility of sperm. TLR7 and TLR8 are encoded by X-chromosome, which suggests that TLR7 and/or TLR8 are only detected in X-sperm. Thus, the involvement was examined as describe below.

(Observation of Localized Expression of TLR7 in Various Mammalian Sperm)

Mouse, bovine, pig, and goat sperm were immunostained and observed for localized expression of TLR7. An image of mouse sperm is shown in (A) of FIG. 1, an image of bovine sperm is shown in (B), an image of pig sperm is shown in (C), and an image of goat sperm is shown in (D).

Figure 1:
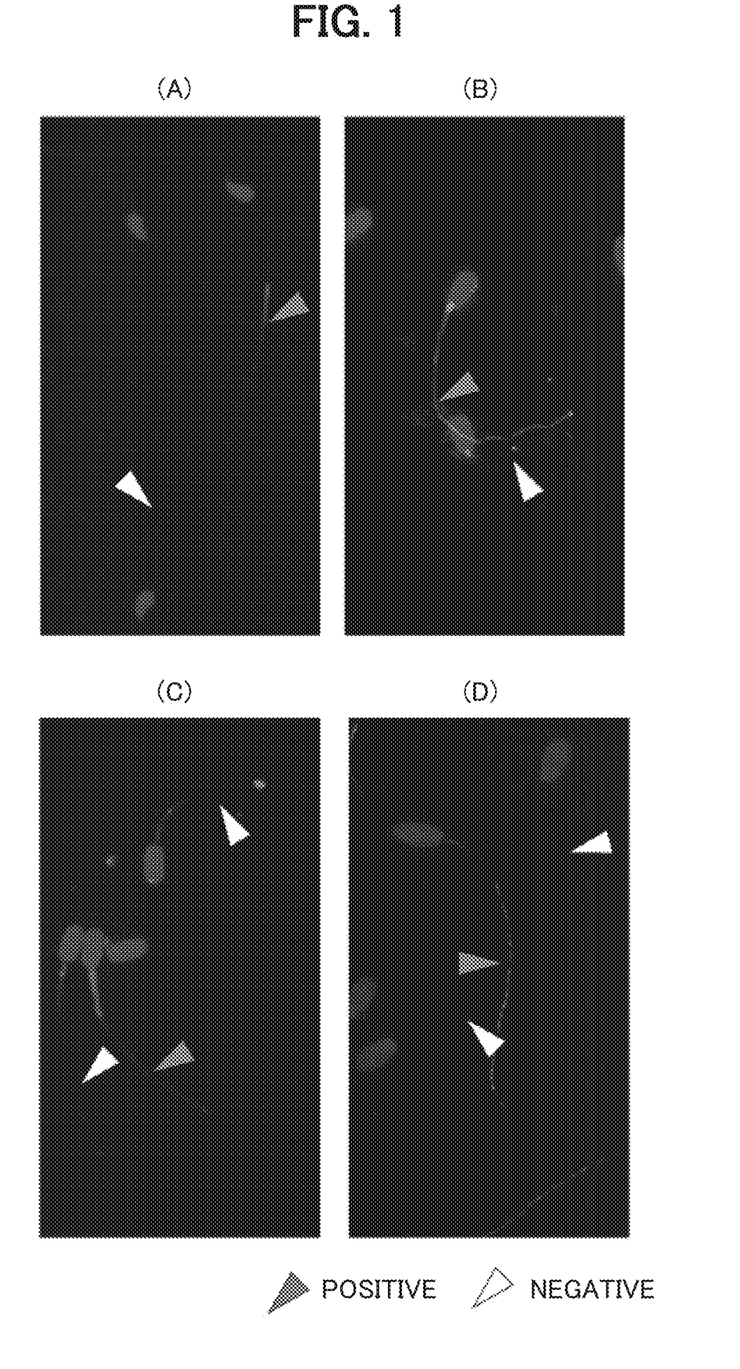
FIG. 1 illustrates in (A) to (D) images showing localization of TLR7 in sperm from various animals.

As shown in (A) to (D) of FIG. 1, TLR7 was expressed in all of the animal species, and TLR7 expression was localized in the sperm tail.

Figure 2:
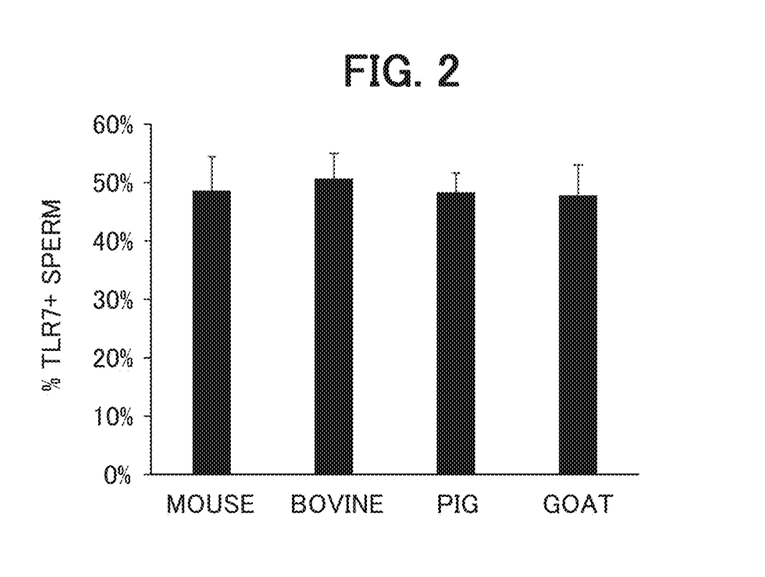
FIG. 2 is a graph showing the percentages of TLR7-positive sperm for the animals.

The percentage of positive sperm expressing TLR7 was determined. The results are shown in FIG. 2. As shown in FIG. 2, the percentages of positive sperm expressing TLR7 are around 50% in all of the animal species. The results suggest that only X chromosome-bearing sperm express TLR7.

(Examination of Effect of TLR7 Ligand on Sperm)

Effects of a TLR7 ligand on sperm were examined by incubating various mammalian sperm in a medium supplemented with the TLR7 ligand.

(Examination in Mouse Sperm)

Mouse sperm were incubated in a medium prepared by adding albumin and a TLR7 ligand to an embryo culture medium (HTF) at 37° C., 5% $CO_2$ for 1 hour. The TLR7 ligand used was Resiquimod R-848 (hereinafter referred to as R-848). The content of R-848 was 0 µM, 0.003 µM, 0.03 µM, 0.3 µM, 1.5 µM, or 3 µM.

Figure 3:
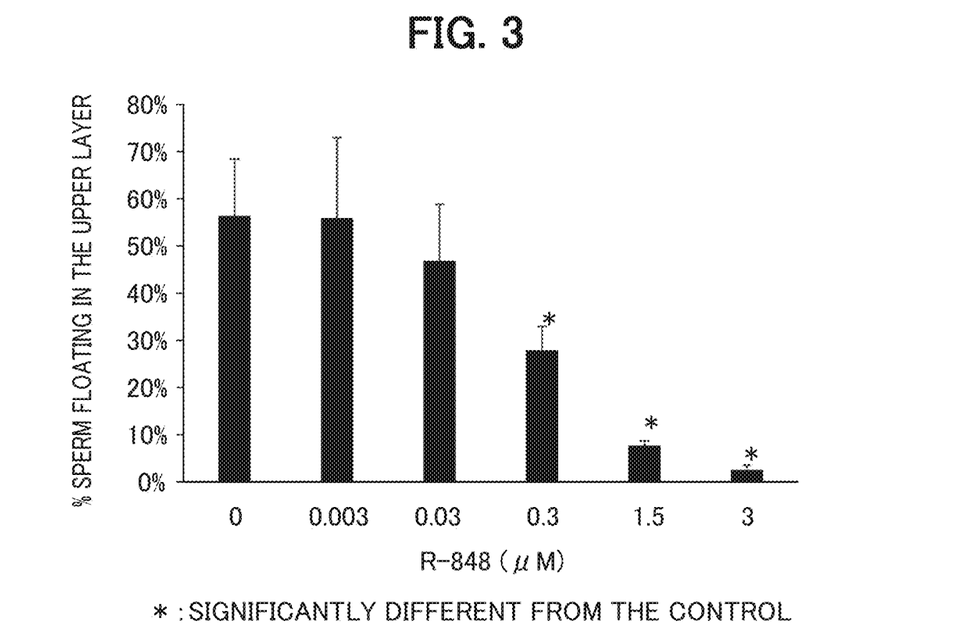
FIG. 3 is a graph showing the percentages of floating sperm when mouse sperm were incubated in a medium supplemented with a TLR7 ligand.

FIG. 3 shows the percentage of sperm floating in the upper layer of the medium. As shown in FIG. 3, the percentage of sperm floating in the upper layer decreases depending on the concentration of R-848, and the percentage of the sperm in the 0.3 µM treatment group was halved compared to the non-treatment group.

The sperm floating in the upper layer were collected, and DNA was extracted. Then, the percentages of X chromosome-bearing sperm (hereinafter referred to as X-sperm) and Y chromosome-bearing sperm (hereinafter referred to as Y-sperm) were determined by real-time PCR (polymerase chain reaction).

Figure 4:
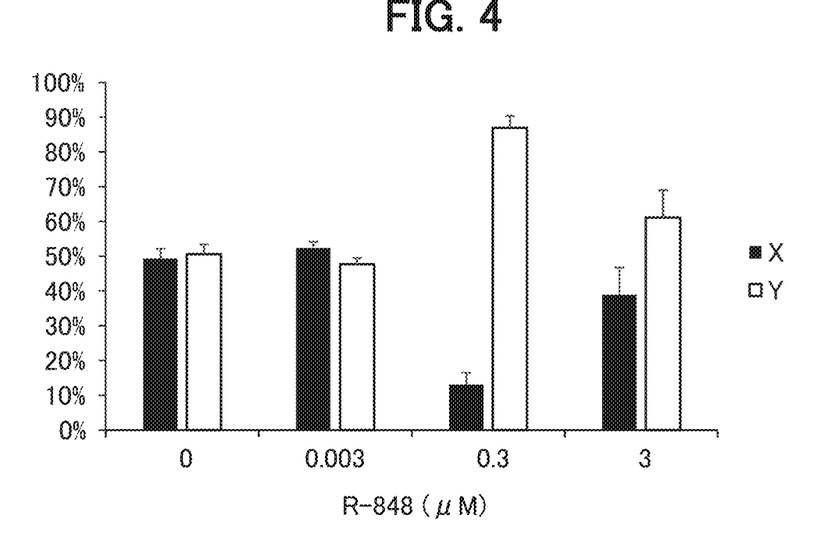
FIG. 4 is a graph showing the percentages of X chromosome-bearing sperm and Y chromosome-bearing sperm in floating sperm when mouse sperm were incubated in a medium supplemented with a TLR7 ligand.

The results are shown in FIG. 4. As shown in FIG. 4, the 0.3 and 3 µM treatment groups showed higher percentage of Y-sperm, and particularly the 0.3 µM treatment group showed 80% or more of Y-sperm.

The floating sperm in the non-treatment group and 0.3 µM treatment group were washed, and then subjected to in vitro fertilization. The percentage of in vitro fertilization embryo bearing XX chromosomes or XY chromosomes was determined. The results are shown in Table 2.

TABLE 2

|  | Number of embryos tested | (Number) | | (%) | |
| --- | --- | --- | --- | --- | --- |
|  |  | XX chromosomes | XY chromosomes | XX chromosomes | XY chromosomes |
| Non-treatment group | 132 | 70 | 62 | 53 | 47 |
| 0.3 µM treatment group | 98 | 13 | 85 | 13 | 87 |

As shown in Table 2, the percentages of XX chromosomes and XY chromosomes were almost the same when the floating sperm from the non-treatment group was used, while about 90% of the fertilized eggs bore XY chromosomes when the floating sperm from the 0.3 µM treatment group was used. In addition, when blastocyst embryos derived from in vitro fertilization using the floating sperm from 0.3 µM treatment group were transferred, 10 of 12 newborns were born as male.

(Examination in Bovine Sperm)

A frozen bovine semen provided by the Oita Prefectural Agriculture, Forestry and Fisheries Research Center was used. The frozen sperm were melted, and washed with an albumin-free HTF medium. The bovine sperm were incubated in a medium prepared by adding albumin and a TLR7 ligand to HTF at 37° C., 5% $CO_2$ for 1 hour. The TLR7 ligand used was R-848 or imiquimod R-837 (hereinafter referred to as R-837). The content of R-848 was 0 µM, 0.003 µM, 0.03 µM, 0.3 µM, or 3 µM. The content of R-837 was 0.003 µM, 0.03 µM, 0.3 µM, 3 µM, 30 µM, or 300 µM.

Figure 5:
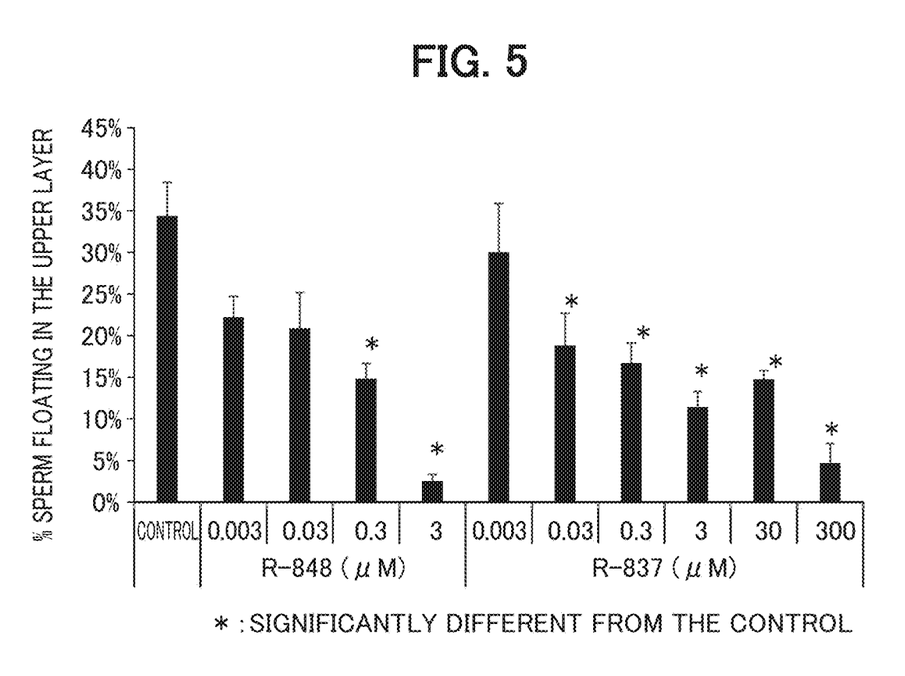
FIG. 5 is a graph showing the percentages of floating sperm when bovine sperm were incubated in a medium supplemented with a TLR7 ligand.

FIG. 5 shows the percentages of floating sperm in incubation of bovine sperm. As shown in FIG. 5, when the sperm were incubated in the presence of a TLR7 ligand, the percentages of floating sperm in the upper layer were decreased in all cases as compared to the non-treatment group.

Then, after collecting the floating sperm in the upper layer and extracting DNA, the percentages of X-sperm and Y-sperm were determined by real-time PCR.

Figure 6:
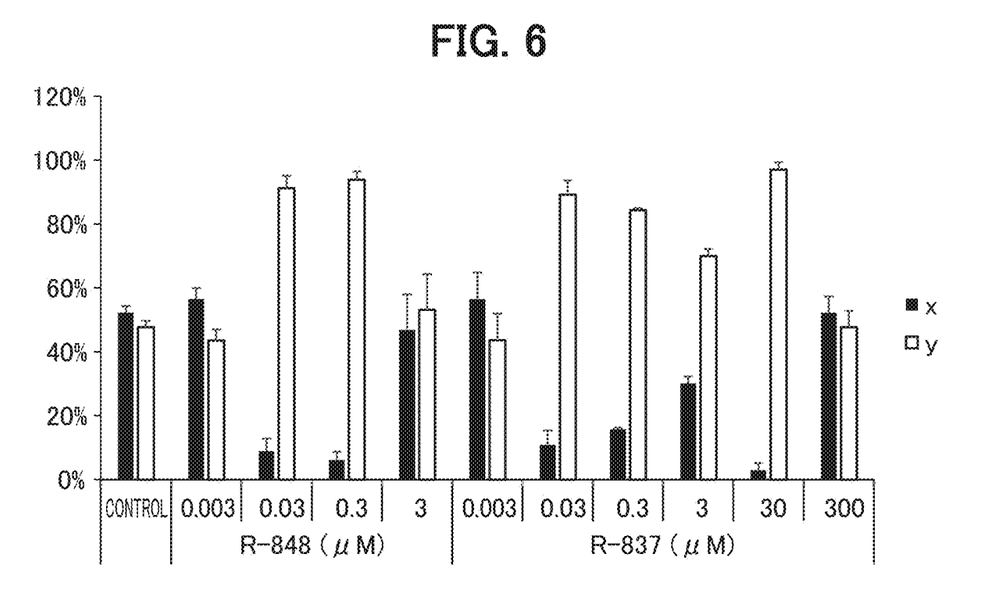
FIG. 6 is a graph showing the percentages of X chromosome-bearing sperm and Y chromosome-bearing sperm in floating sperm when bovine sperm were incubated in a medium supplemented with a TLR7 ligand.

FIG. 6 shows the percentages of X-sperm and Y-sperm in the floating sperm. As shown in FIG. 6, in the R-848 treatment groups, the 0.03 to 3 µM treatment groups showed higher percentage of Y-sperm, and particularly the 0.03 to 0.3 µM treatment groups showed 90% or more of Y-sperm. On the other hand, in the R-837 treatment groups, the 0.03 to 30 µM treatment groups showed higher percentage of Y-sperm, showing 70% or more of Y-sperm.

Bovine in vitro fertilization was performed using the sperm in the upper layer rich in Y-sperm from the 0.03 µM R-848 treatment group. This resulted in 71.7% of fertilization rate and 64.3% of blastocyst embryo transfer rate, which are comparable to those of usual in vitro fertilization, meaning good fertilization rate.

Next, sexing of the blastocyst embryos was performed by real-time PCR. This resulted in 87.8% of male embryos. Therefore, it was demonstrated that male newborns can selectively be obtained in cattle.

(Examination in Pig Sperm)

Pig sperm were incubated in a medium prepared by adding cysteine, glycine, and a TLR7 ligand to the Modena solution at 37° C., 5% $CO_2$, 5% $O_2$ for 2 hours. The TLR7 ligand used was R-848. The content of R-848 was 0 µM or 0.3 µM.

Figure 7:
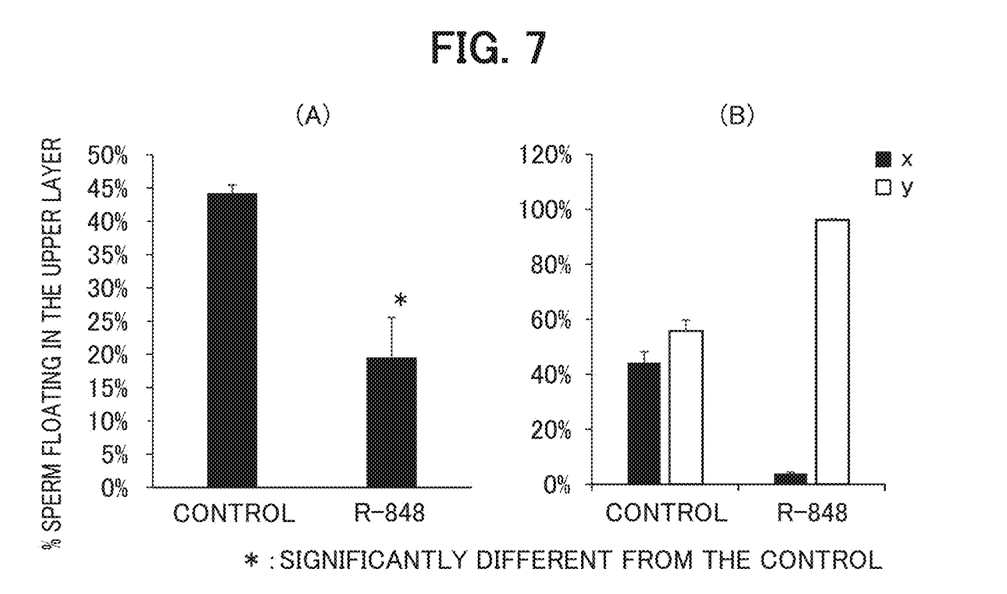
FIG. 7 shows a graph showing the percentage of floating sperm in (A) and a graph showing the percentages of X chromosome-bearing sperm and Y chromosome-bearing sperm in floating sperm in (B), when pig sperm were incubated in a medium supplemented with a TLR7 ligand.

FIG. 7 shows in (A) the percentages of floating sperm in incubation of pig sperm. As shown in (A) of FIG. 7, when the sperm were incubated in the presence of the TLR7 ligand, the percentage of floating sperm in the upper layer were decreased by half as compared to the non-treatment group.

After collecting the floating sperm in the upper layer and extracting DNA, the percentages of X-sperm and Y-sperm were determined by real-time PCR.

FIG. 7 shows in (B) the percentages of X-sperm and Y-sperm in the floating sperm. As shown in (B) of FIG. 7, the TLR7 ligand treatment group showed 90% or more of Y-sperm. Artificial insemination was performed using the floating sperm suspended in HIRO-SWINE B, resulting in 6 males of 7 newborns.

From the examination results as described above, it was demonstrated that Y chromosome-bearing sperm can be separated off, and artificial insemination or in vitro fertilization using the sperm can result in male preselection in mammals such as domestic animals.

(Examination of Separation by Hypergravity Load)

Mouse sperm were separated by loading hypergravity, and its effect was examined.

Mouse sperm were incubated in a medium (500 µL) prepared by adding albumin and a TLR7 ligand to an embryo culture medium (HTF) at 37° C., 5% $CO_2$ for 1 hour. The TLR7 ligand used was Resiquimod R-848 (hereinafter referred to as R-848). The content of R-848 was 0.3 µM.

After 30 minutes, the media were centrifuged using a centrifuge (product name: Tabletop Micro Refrigerated Centrifuge Model 3520, produced by KUBOTA Corporation Co., Ltd.) at 37° C. for 30 minutes. The centrifugation was at a centrifugal force of 50×g, 100×g, or 500×g. For comparison, a system without centrifugation (0×g) was also prepared.

After centrifugation, 150 µL of the upper layer (30% of the upper layer) of each of the media was collected, and the percentages of X-sperm and Y-sperm in each of the media were determined in the same manner as described above. The results are shown in FIG. 8.

In addition, 150 µL of the lower layer (30% of the lower layer) of each of the media was collected, and the percentages of X-sperm and Y-sperm in each of the media were determined in the same manner as described above. The results are shown in FIG. 9.

Figure 8:
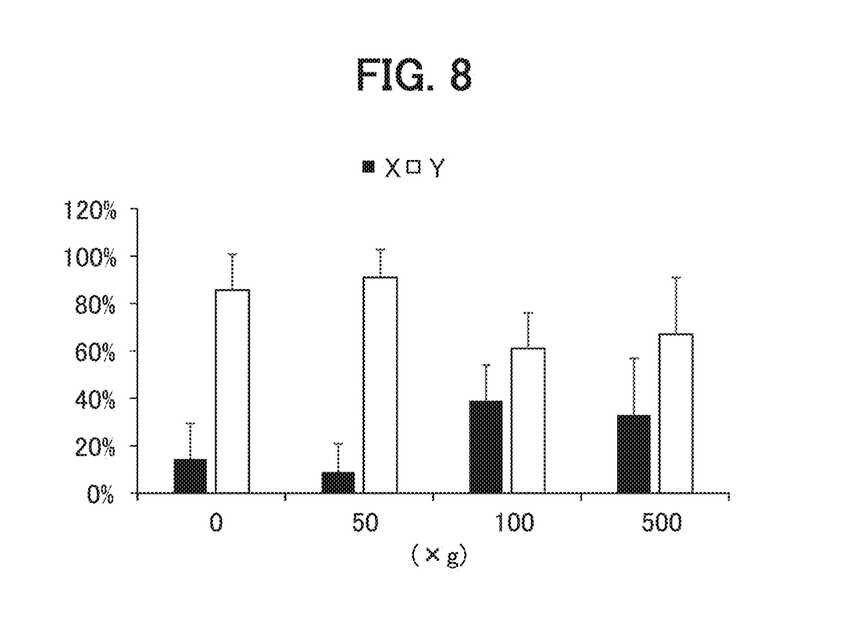
FIG. 8 is a graph showing the percentages of X chromosome-bearing sperm and Y chromosome-bearing sperm present in the upper layer of a medium when mouse sperm were incubated in the medium supplemented with a TLR7 ligand and separated by centrifugation.

As shown in FIG. 8, the sperm population in the upper layer of the medium had a percentage of Y-sperm exceeding 80% when centrifuged at 0×g or 50×g. In particular, the sperm population centrifuged at 50×g achieved about 90% of Y-sperm. However, centrifugation at 100×g or more resulted in about 60%.

Figure 9:
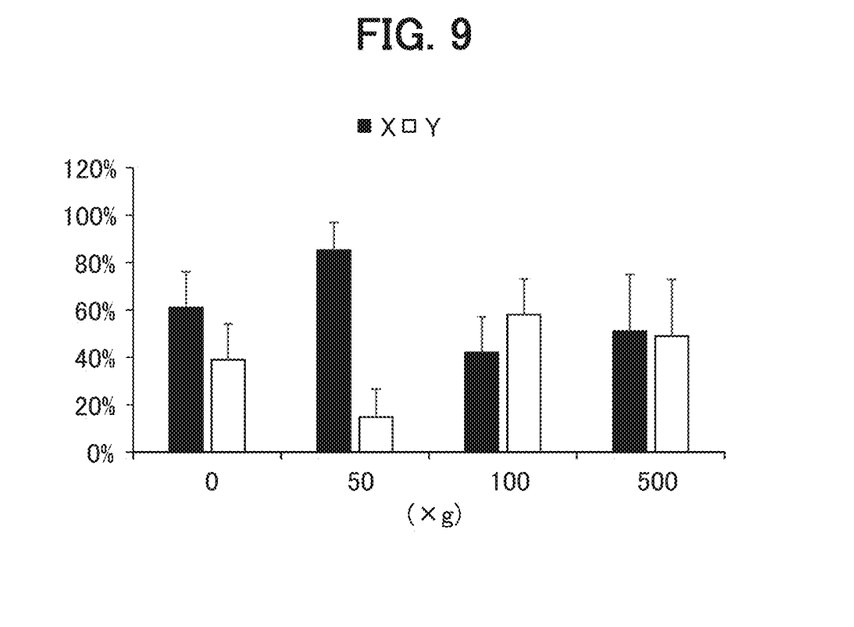
FIG. 9 is a graph showing the percentages of X chromosome-bearing sperm and Y chromosome-bearing sperm present in the upper layer of a medium when mouse sperm were incubated in the medium supplemented with a TLR7 ligand and separated by centrifugation.

As shown in FIG. 9, the sperm population in the lower layer of the medium had a percentage of X-sperm exceeding 60% when centrifuged at 0×g or 50×g. In particular, the sperm population centrifuged at 50×g achieved near 90% of X-sperm. However, when centrifugation is performed at 100×g or more, the sperm population had a percentage of X-sperm below 50%.

These results showed that separation by loading a centrifugal force of more than 0×g and less than 100×g, more preferably 50×g, can effectively separate the sperm population rich in Y-sperm and the sperm population rich in X-sperm.

(In Vitro Fertilization)

A sperm population in the upper layer (upper layer group) and a sperm population in the lower layer (lower layer group) which had been separated by loading a centrifugal force of 50×g as described above were subjected to in vitro fertilization to form blastocyst embryos. Then, the percentages of blastocyst embryos bearing XX chromosomes or XY chromosomes were determined. In addition, a sperm population obtained by incubating in the same medium as described above at 37° C. for 60 minutes without addition of the TLR7 ligand and without centrifugation (non-treatment group) was subjected to in vitro fertilization in the same manner as described above to form a blastocyst embryo. Then, the percentages of blastocyst embryos bearing XX chromosomes or XY chromosomes were determined.

The results are shown in Table 3. In the column "2-cell" in Table 3, "number" represents number of observed cleavages in 24 hours, while "%" represents "(number of 2-cell/number of eggs)×100." In the column "blastocyst embryo," "number" represents number of formed blastocyst embryos, while "%" represents "(number of blastocyst embryos/number of 2-cell)×100."

TABLE 3

| | Egg | 2-cell | | Blastocyst embryo | | XX chromosomes | | XY chromosomes | |
|---|---|---|---|---|---|---|---|---|---|
| | (number) | (number) | (%) | (number) | (%) | (number) | (%) | (number) | (%) |
| Non-treatment group | 82 | 62 | 76 | 46 | 74 | 22 | 48 | 24 | 52 |
| Upper layer group | 103 | 81 | 79 | 59 | 73 | 6 | 10 | 53 | 90 |
| Lower layer group | 99 | 69 | 70 | 48 | 70 | 39 | 81 | 9 | 19 |

The non-treatment group, the upper layer group, and the lower layer group showed the same rate of occurrence of 2-cell and blastocyst embryo without significant difference. This demonstrated that centrifugation on sperm that had been incubated in a medium supplemented with a TLR7 ligand had no effect on the fertilization function of the sperm.

The percentages of XX chromosomes and XY chromosomes of the blastocyst embryo in the non-treatment group were each about 50%, suggesting that, when the blastocyst embryo is subjected to in vitro fertilization or the like, male and female newborns would be born in about the same percentages.

On the other hand, the upper layer group showed 90% of blastocyst embryos bearing Y chromosome, suggesting that, when the blastocyst embryo is subjected to in vitro fertilization or the like, 90% of newborns would be born as male. In contrast, the lower layer group showed 81% of blastocyst embryos bearing X chromosome only, suggesting that, when the blastocyst embryo is subjected to in vitro fertilization or the like, 81% of newborns would be born as female.

As described above, separation of sperm through overloading resulted in successful separation of a sperm population rich in X chromosome-bearing sperm and a sperm population rich in Y chromosome-bearing sperm with high accuracy, suggesting that use of the sperm populations for artificial insemination or in vitro fertilization can provide sex-preselected, male or female, newborns.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2017-129768, filed on Jun. 30, 2017, and Japanese Patent Application No. 2018-120260, filed on Jun. 25, 2018, of which the entirety of the disclosures of is incorporated by reference herein.

INDUSTRIAL APPLICABILITY

The method for separating mammalian sperm according to the present disclosure can separate Y chromosome-bearing sperm and X chromosome-bearing sperm, enabling gender preselection of newborns in artificial insemination or in vitro fertilization, which is available in the domestic animal industry and the like.

The invention claimed is:

1. A method for separating mammalian sperm, comprising incubating the sperm in a medium containing a TLR7 ligand; and
separating the sperm into a population of X chromosome-bearing sperm that is sunk and a population of Y chromosome-bearing sperm that is floating, wherein
the TLR7 ligand causes the population of the X chromosome-bearing sperm that is to show a decrease in sperm activity in response to the TLR7 ligand to sink, and
the population of the Y chromosome-bearing sperm that is less likely to show a decrease in sperm activity in response to the TLR7 ligand floats upward.

2. The method for separating mammalian sperm according to claim 1, wherein the TLR7 ligand is at least one selected from the group consisting of resiquimod, imiquimod, gardiquimod, and loxoribine.

3. The method for separating mammalian sperm according to claim 1, wherein the TLR7 ligand is added in an amount from 0.03 to 30 μM.

4. The method for separating mammalian sperm according to claim 1, wherein the sperm are separated by hypergravity load.

5. The method for separating mammalian sperm according to claim 4, wherein the hypergravity load is generated by a centrifugal force.

6. The method for separating mammalian sperm according to claim 4, comprising collecting 30% of an upper layer of the medium to obtain a sperm population rich in the Y chromosome-bearing sperm.

7. The method for separating mammalian sperm according to claim 4, comprising collecting 30% of a lower layer of the medium to obtain a sperm population rich in the X chromosome-bearing sperm.

8. The method of claim 1 wherein the mammalian sperm is from a non-human mammal, and further comprising:
   after separating the sperm, performing artificial insemination for the non-human mammal using the separated sperm of the non-human mammal.

9. The method of claim 1 wherein the mammalian sperm is from a non-human mammal, and further comprising:
   performing in vitro fertilization for the non-human mammal using sperm of the non-human mammal.

* * * * *